United States Patent
Zweig

(10) Patent No.: US 9,751,966 B2
(45) Date of Patent: Sep. 5, 2017

(54) RAPID CURE POLYMERIC RESINS

(71) Applicant: THE BOEING COMPANY, Chicago, IL (US)

(72) Inventor: Andrew M. Zweig, Ellisville, MO (US)

(73) Assignee: THE BOEING COMPANY, Chicago, IL (US)

( * ) Notice: Subject to any disclaimer, the term of this patent is extended or adjusted under 35 U.S.C. 154(b) by 161 days.

(21) Appl. No.: 14/924,079

(22) Filed: Oct. 27, 2015

(65) Prior Publication Data

US 2016/0177000 A1    Jun. 23, 2016

Related U.S. Application Data

(60) Provisional application No. 62/095,371, filed on Dec. 22, 2014.

(51) Int. Cl.
| | | |
|---|---|---|
| *C08F 212/34* | (2006.01) | |
| *C07C 319/18* | (2006.01) | |
| *C07C 323/12* | (2006.01) | |
| *C08F 12/22* | (2006.01) | |
| *C08F 12/30* | (2006.01) | |
| *C08F 12/34* | (2006.01) | |

(52) U.S. Cl.
CPC .......... *C08F 212/34* (2013.01); *C07C 323/12* (2013.01); *C08F 12/22* (2013.01); *C08F 12/30* (2013.01); *C08F 12/34* (2013.01)

(58) Field of Classification Search
CPC ........ C07C 323/12; C08F 12/22; C08F 12/30; C08F 12/34; C08F 212/34
USPC ........................................................ 526/289
See application file for complete search history.

(56) References Cited

U.S. PATENT DOCUMENTS

| | | | |
|---|---|---|---|
| 4,692,500 A | * | 9/1987 | Hefner, Jr. ............ C08F 283/10 525/529 |
| 5,955,206 A | | 9/1999 | Okazaki et al. |
| 8,029,910 B2 | | 10/2011 | Ikuta et al. |
| 8,389,630 B2 | | 3/2013 | Tamai et al. |
| 2003/0062125 A1 | | 4/2003 | Takamatsu et al. |

FOREIGN PATENT DOCUMENTS

| | | |
|---|---|---|
| WO | 2011033262 A1 | 3/2011 |
| WO | 2012100980 A1 | 8/2012 |

OTHER PUBLICATIONS

Mark Caddy, Modified Liquid Polysulfide Polymers; their Preparation, Characterisation, Photocuring and Potential Photoapplications, Department of Chemistry, University of Warwick, Aug. 2001, 188 pp.

* cited by examiner

*Primary Examiner* — Ling Choi
*Assistant Examiner* — Chun-Cheng Wang
(74) *Attorney, Agent, or Firm* — Patterson + Sheridan, LLP

(57) ABSTRACT

A polysulfide material having reactive vinyl end groups and a method of making a vinyl end-capped polysulfide material are described. The vinyl end-capped polysulfide material has potential applications as a sealant, an adhesive, a coating, a caulking, or the like. In a specific example, the polysulfide material may be used as a precursor material for a sealant resin in the manufacturing of an integral fuel tank of an aircraft. An example method for making polysulfide materials includes contacting a vinyl-functionalized aryl halide and/or a vinyl-functionalized heteroaryl halide with dithiols and/or trithiols in the presence of an organic solvent.

19 Claims, 4 Drawing Sheets

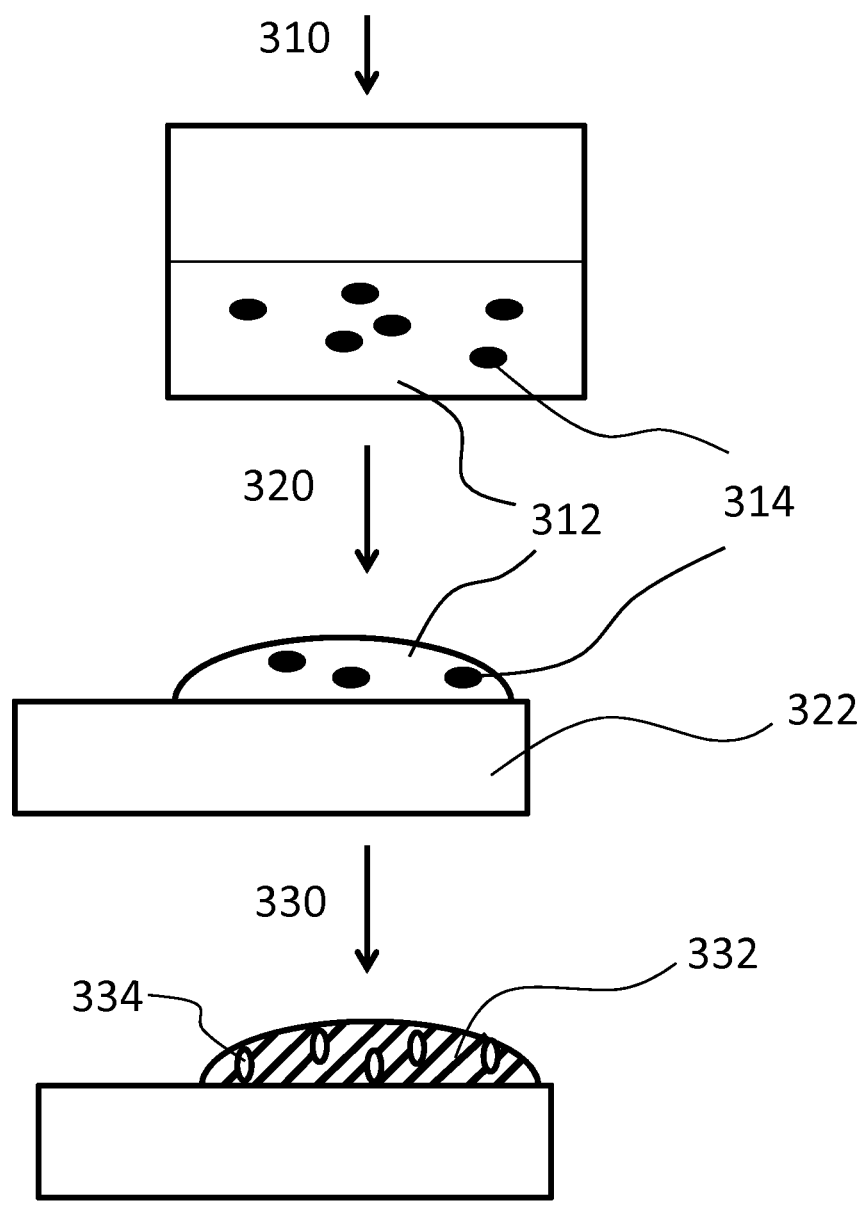

RAPID CURE POLYMERIC RESINS

CROSS-REFERENCE TO RELATED APPLICATIONS

This application claims benefit from U.S. Provisional Patent Application No. 62/095,371, filed Dec. 22, 2014, which is incorporated by reference in its entirety.

FIELD

The present disclosure relates generally to polymeric resins useful for adhesive and sealant applications, and more specifically to polysulfide materials useful for adhesive and sealant applications.

BACKGROUND

In general, polysulfide resins find uses in any application requiring a strongly adhering surface coating or strong adhesion between materials. In aerospace manufacturing, polysulfide resins are used in a variety of applications, such as sealants for fuel tanks, wet-installed fasteners, formation of fillet and fay joints, and aero-smoothing at the wing-to-body joint. Polysulfide resins are also used as adhesives, sealants, coatings, and caulks in other applications such as building construction, manufacturing of automotive components, and fabrication of marine components. In a specific application, polysulfide resins are used as sealants for the formation of integral fuel tanks within, for example, portions of the wing assembly of airplanes or the fuselage of a rotorcraft. In these various applications, the resins currently used as adhesive and sealant materials generally cure relatively slowly via an oxidative process. For example, various polysulfide-based sealants in current use in aerospace applications cure at a rate that is on the order of days or hours rather than minutes. Slow cure rates for adhesives, sealants, coatings, and caulk tend to limit manufacturing throughput.

To achieve faster cure rates, various photopolymerizable resin materials have been proposed, but, in general, these materials have produced unsatisfactory results for reasons such as difficulty in photocuring thick films and/or inferior chemical and mechanical characteristics for intended end uses. Additionally, these photopolymerizable resins often have a short shelf life or are difficult to handle and process. It would be desirable to provide faster curing resin materials having similar (or improved) chemical and/or mechanical characteristics as compared to presently available polysulfide resins.

SUMMARY

In one aspect of the present disclosure, a polysulfide material is described. The polysulfide material is of formula (I):

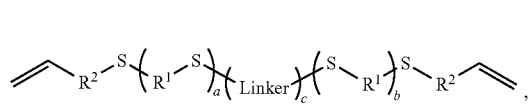

wherein:
each instance of $R^1$ is -alkyl-O-alkyl-O-alkyl-;
each instance of $R^2$ is the same or different and is selected from -aryl-alkyl-,

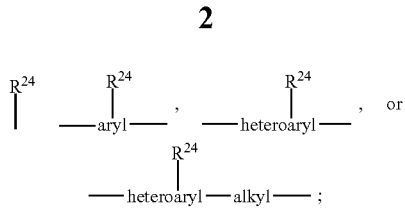

each instance of $R^{24}$ is the same or different and is selected from hydrogen (H), alkyl, or alkoxy;
"Linker" is of formula (II):

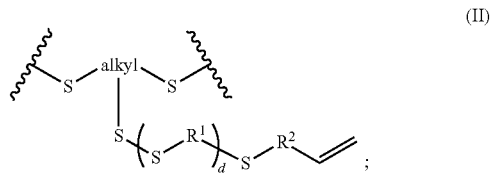

c is less than 1.0 (and represents the fraction of molecules in the polymer having the Linker);
d is 0 when c is 0; and
a+b+d is from about 7 to about 38.

According to another aspect of the present disclosure, a method of making a polysulfide polymer comprises forming a reaction mixture by contacting:
a compound of formula (III):

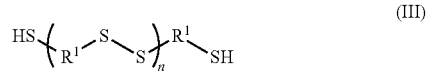

a compound of formula (IV):

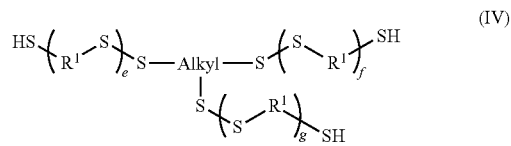

and a compound of formula (V):

wherein:
the contacting of the compounds occurs in the presence of an organic solvent;
each instance of $R^1$ is -alkyl-O-alkyl-O-alkyl-;
$R^2$ is

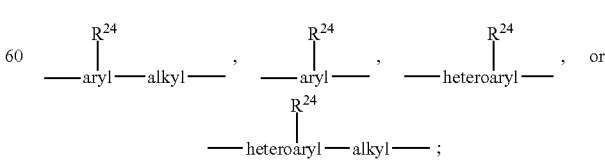

each instance of $R^{24}$ is the same or different and is selected from hydrogen (H), alkyl, or alkoxy;

X is halo:

n is from about 7 to about 38; and e+f+g is from about 7 to about 38.

In some aspects, a polymer blend includes a first polymer and a second polymer. The first polymer is of formula (I):

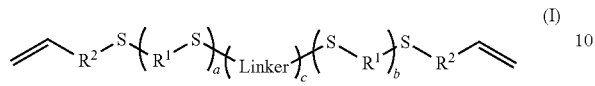
(I)

wherein:

each instance of $R^1$ is -alkyl-O-alkyl-O-alkyl-, each instance of $R^2$ is the same or different and is selected from

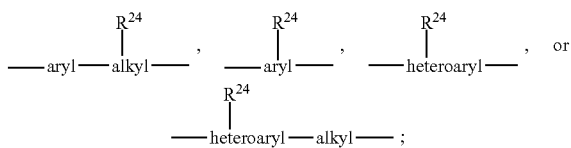

each instance of $R^{24}$ is the same or different and is selected from hydrogen (H), alkyl, or alkoxy;

"Linker" is of formula (II):

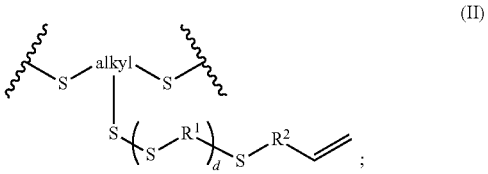
(II)

c is less than 1.0 but greater than 0, and a+b+d is from about 7 to about 38.

The second polymer is of formula (I):

(I)

wherein:

$R^1$ is -alkyl-O-alkyl-O-alkyl-;

each instance of $R^2$ is the same or different and is selected from

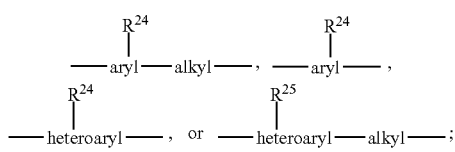

each instance of $R^{24}$ is the same or different and is selected from hydrogen (H), alkyl, or alkoxy;

"Linker" is of formula (II):

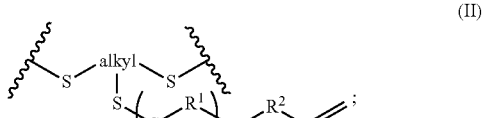
(II)

c=0, d=0, and a+b is from about 7 to about 38.

BRIEF DESCRIPTION OF ILLUSTRATIONS

FIG. 3 depicts a method of manufacturing using a polysulfide material having reactive vinyl groups end groups.

DETAILED DESCRIPTION

Figure 1A:
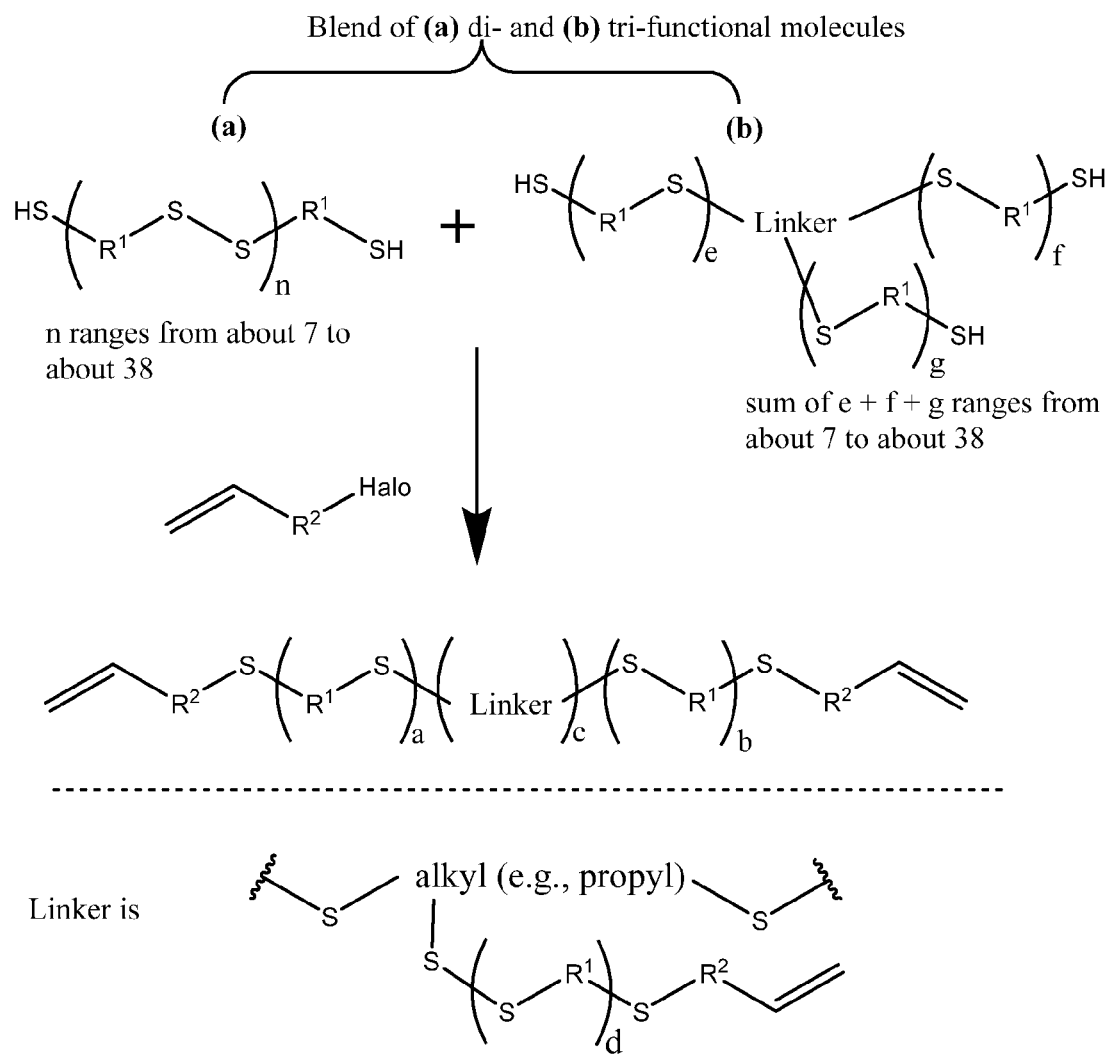
FIGS. 1A and 1B depicts schemes for preparing a polysulfide material having reactive vinyl end groups.

With reference now to FIG. 1A, a preparation scheme for polysulfide materials (polymers and/or oligomers) with reactive vinyl end groups is depicted. As will be discussed further, vinyl end-capped polysulfides can be cured/polymerized using radical and/or cationic initiated processes and thus may be photocured using, for example, ultraviolet-light sensitive free radical generators or photo-acid generators.

The reaction scheme depicted in FIG. 1A produces a polysulfide material of formula (I):

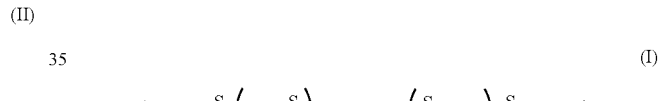
(I)

wherein:

$R^1$ is -alkyl-O-alkyl-O-alkyl-;

each instance of $R^2$ is the same or different and is selected from

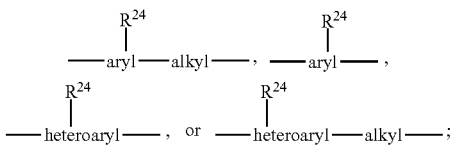

each instance of $R^{24}$ is the same or different and is selected from hydrogen (H), alkyl, or alkoxy;

"Linker" is of formula (II):

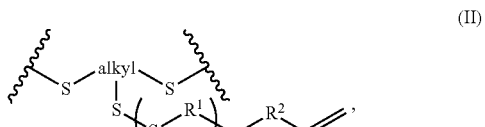
(II)

c is less than 1.0 and represents the fraction of molecules in the polymer having the Linker; d is 0 when c is 0; and a+b+d is from about 7 to about 38. Each "alkyl" moiety within the polysulfide of formula (I) (which includes formula (II)) may include 1 to 20 carbons ($C_{1-20}$). In some aspects, each "alkyl" within the polysulfide material of formula (I) may include 1 to 5 carbon atoms ($C_{1-5}$). In some aspects, each "alkyl" moiety within the polysulfide material of formula (I) is one of -methyl-($C_1$), -ethyl-($C_2$), and -propyl-($C_3$). Furthermore, each instance of an "alkyl" moiety within formula (I) (and formula (II)) may be independently selected. That is, "alkyl" moieties at different positions in the polysulfide material of formula (I) are not required to include the same number of carbons or have the same structure. For example, each $R^1$ may be -ethyl-O-methyl-O-ethyl- and the "alkyl" moiety in "Linker" group may be -propyl-($C_3$). $R^{24}$ may be hydrogen, alkyl, or alkoxy. "Alkyl" for $R^{24}$ includes, but is not limited to, methyl, ethyl, propyl, butyl, and pentyl.

In the preparation scheme depicted in FIG. 1A, a compound corresponding to formula (I) is prepared by contacting:

a compound of formula (III):

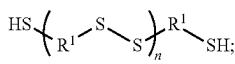
(III)

a compound of formula (IV):

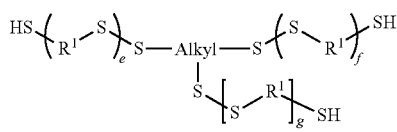
(IV)

and a compound of formula (V):

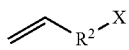
(V)

wherein:
the contacting of the compounds occurs in the presence of an organic solvent; $R^1$ is -alkyl-O-alkyl-O-alkyl-;
each instance of $R^2$ is the same or different and is selected from

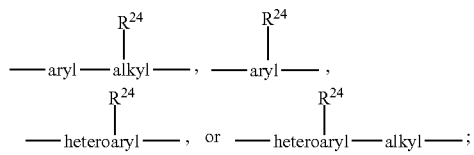

each instance of $R^{24}$ is the same or different and is selected from hydrogen (H), alkyl, or alkoxy;

X is halo;

n is from about 7 to about 38; and e+f+g is from about 7 to about 38. A plurality of different compounds of formula (V) may be included in the reaction mixture such that different $R^2$ groups may be independently incorporated into the final product.

Figure 1B:
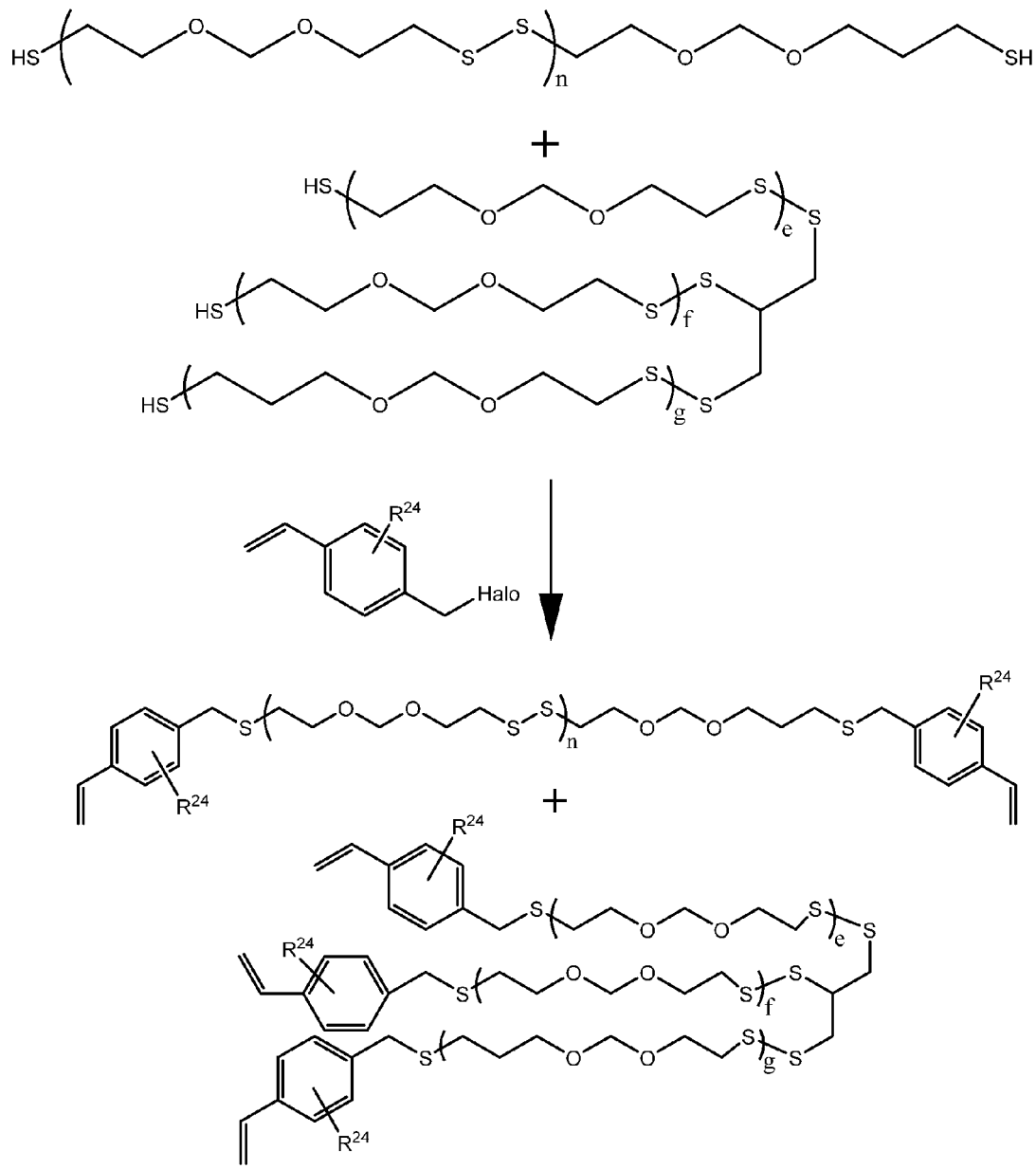

FIG. 1B depicts a scheme for synthesizing a particular example of a polysulfide material corresponding to formula (I).

In the scheme of FIG. 1B, a compound of formula (VI):

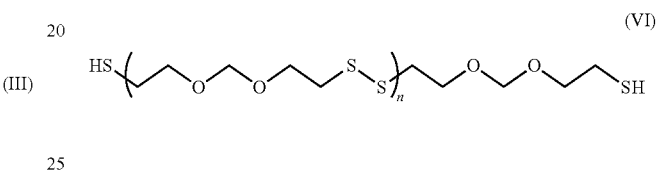
(VI)

corresponds to the compound of formula (II). In formula (VI), n ranges from about 7 to about 38. The compound of formula (VI) and a compound of formula (VII) are contacted with a compound of formula (VIII):

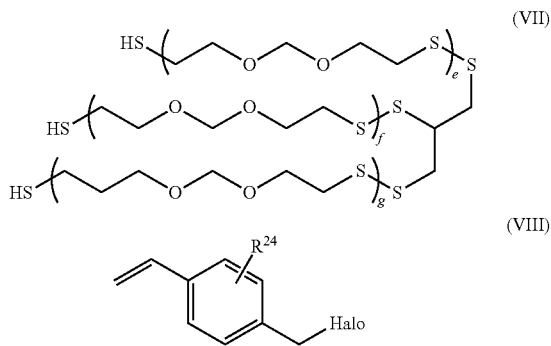
(VII)

(VIII)

In formula (VII), the sum e+f+g ranges from about 7 to about 38. In formula (VIII), each instance of $R^{24}$ is the same or different and is selected from hydrogen (H), alkoxy, or alkyl. The reaction scheme of FIG. 1B may produce a mixture of different compounds corresponding to formula (IX) and/or formula (X):

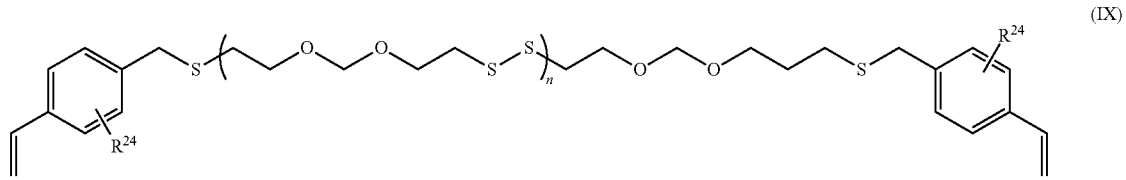
(IX)

-continued

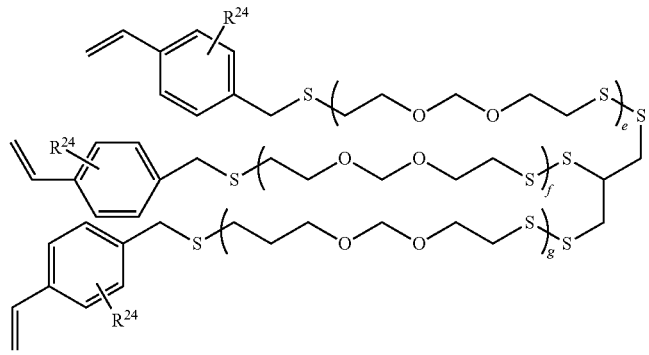

(X)

The relative amounts of compounds corresponding to formula (IX) and formula (X) may depend on the relative amounts of compounds corresponding to formula (VI) and formula (VII) in the initial reaction mixture.

The polysulfide starting materials of formula (III) can be purchased from chemical suppliers such as, for example, Toray Fine Chemicals Co., LTD (e.g., Thiokol® derivatives from the LP product line) (Tokyo, Japan) or AkzoNobel (e.g., Thioplast® G products) (Amsterdam, Netherlands). In addition, polysulfide starting materials of formula (III) can be prepared by routine methods, for example, condensation (under mildly acidic conditions) of halo-alkyl-alcohols (e.g., 3-chloro-1-propanol; 2-chloroethan-1-ol; 4-chloro-1-butanol; 1,2,3-trichloropropane; etc.) with formaldehyde followed by reaction with sodium sulfide. Alternatively, it is known that higher molecular weight di-halo or tri-halo polymeric species can be reacted with sodium polysulfide to yield a mixture of di-thiol(s) and tri-thiol(s). Other processes can involve the reaction of di-alkenes or tri-alkenes with lower molecular weight dithiols to produce a similar range of products. See, e.g., "Polyethers, Part III. Polyalkylene Sulfides and Other Polythioethers," pp. 60-94, Edited by Norman G. Gaylord, Interscience Publishers/John Wiley, New York, 1962. Library of Congress 62-15824.

Figure 2:
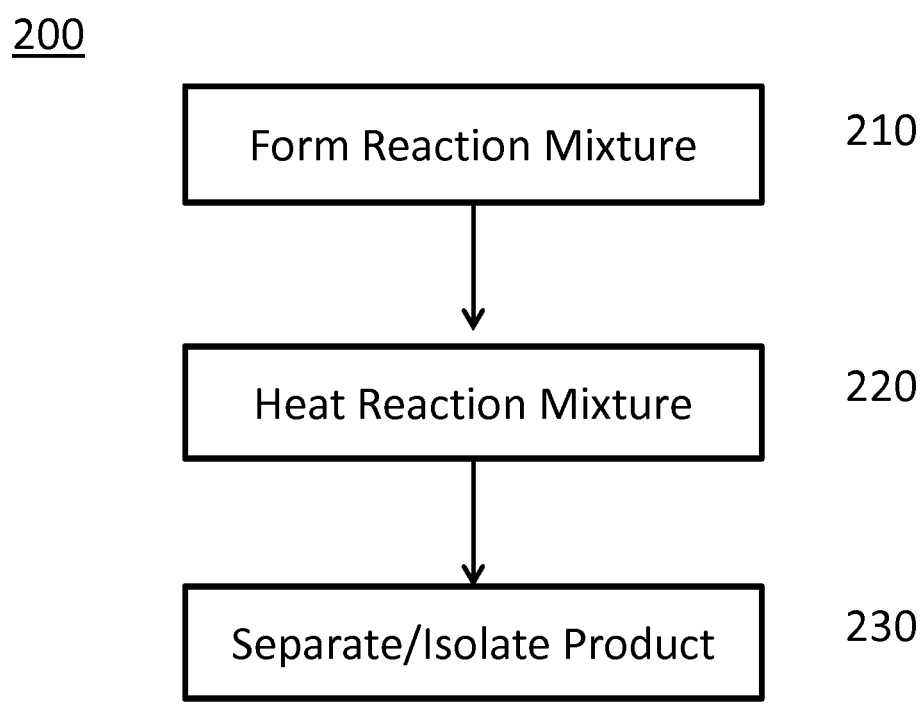
FIG. 2 depicts a method for preparing a polysulfide material having reactive vinyl end groups.

FIG. 2 depicts a first method 200 for preparing a polysulfide material of formula (I), for example.

In element 210 of the first method 200, a reaction mixture is formed. The reaction mixture is formed by contacting disulfide materials and a vinyl-functionalized aryl halide material. The disulfide materials may correspond to compounds of formula (VI), compounds of formula (VII)), or mixtures thereof. The vinyl-functionalized aryl halide corresponds to a compound (or a mixture of compounds) of formula (VIII). In element 210, the vinyl-functionalized aryl halide material may be added to the reaction mixture in increments or dropwise over several minutes. The reaction mixture may be shaken and/or stirred to promote mixing of the various components. The reaction mixture may include solvent or solvents such as organic solvent. An organic solvent such as DMF (N,N-dimethylformamide) is suitable for inclusion in the reaction mixture. Other organic solvents, such as THF (tetrahydrofuran), NMP (N-methylpyrrolidinone), and DMAC (N,N-dimethylacetamide) are also suitable.

In element 220, the reaction mixture is optionally heated. The reaction mixture may be heated to a constant temperature or the temperature of the mixture may be ramped/varied. During element 220, the temperature of the reaction mixture may be approximately 20° C.-100° C. During element 220, the temperature of the reaction mixture may more preferably be in a range from 40° C.-80° C. The reaction mixture may be held at temperature for about 1 minute to about four hours. Element 210 and element 220 may occur simultaneously or otherwise overlap in time—that is, heating may begin during or before the mixing process.

In element 230, a reaction product corresponding to a polysulfide material of formula (I) is separated/isolated from the reaction mixture. Element 230 may comprise various washing, drying, filtering, and solvent extraction steps. Element 230 may include distillation steps, such as vacuum distillation processes. The reaction product may, for example, comprise a mixture of polysulfide materials of formula (IX) and formula (X).

The reaction mixture formed in element 210 may include additional components such as catalysts, oxygen scavengers, additional dithiol, tri- or higher functionalized thiols, solvents, polymerization inhibitors, or the like. A base such as sodium hydroxide (NaOH) may be provided to the reaction mixture for removal/segregation of halide ions formed in the reaction of halide and thiol moieties and/or promote the reaction between halide and thiol moieties. Specific details of an exemplary synthesis of an example compound E1 are provided in a section below.

The first method 200 may be used to prepare a variety of different polysulfide materials. A non-limiting listing of example polysulfide materials that may be prepared is provided in Table I. Examples 1a-50b are described. Each example material corresponds to formula (I). 'c' is less than 1.0 and represents the fraction of molecules in the polymer having the Linker. 'a'+'b'+'c' is from about 7 to about 38.

TABLE I

Example polysulfide materials.

| Ex. | Linker | R² | R¹ |
|---|---|---|---|
| 1a | Absent | (para-phenylene-CH₂) | —ethyl—O—methyl—O—ethyl— |
| 1b | (glyceryl trithioether linker) | | |
| 2a | Absent | (2-methyl-phenylene-CH₂) | —ethyl—O—methyl—O—ethyl— |
| 2b | (glyceryl trithioether linker) | | |
| 3a | Absent | (3-methyl-phenylene-CH₂) | —ethyl—O—methyl—O—ethyl— |
| 3b | (glyceryl trithioether linker) | | |
| 4a | Absent | (2,5-dimethyl-phenylene-CH₂) | —ethyl—O—methyl—O—ethyl— |
| 4b | (glyceryl trithioether linker) | | |

TABLE I-continued
Example polysulfide materials.
$$\diagdown_{R^2}\diagdown S{\left(\diagdown_{R^1}\diagdown S\right)}_a{\left(Linker\right)}_c{\left(S\diagdown_{R^1}\diagdown\right)}_b S\diagdown_{R^2}\diagdown$$
| Ex. | Linker | R² | R¹ |
|---|---|---|---|
| 5a | Absent | 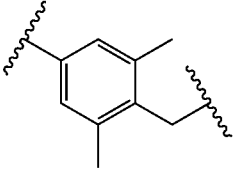 [SMILES: *Cc1c(C)cc(*)cc1C] | —ethyl—O—methyl—O—ethyl— |
| 5b | 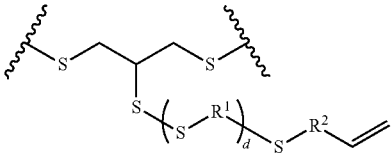 | | |
| 6a | Absent | 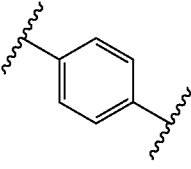 [SMILES: *c1ccc(*)cc1] | —ethyl—O—methyl—O—ethyl— |
| 6b | 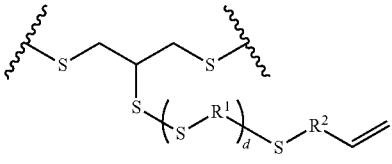 | | |
| 7a | Absent | 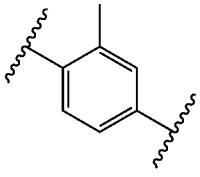 [SMILES: *c1ccc(*)c(C)c1] | —ethyl—O—methyl—O—ethyl— |
| 7b | 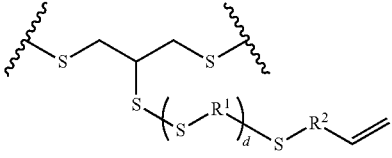 | | |
| 8a | Absent | 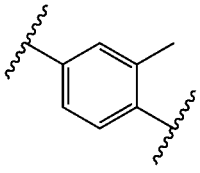 [SMILES: *c1ccc(*)c(C)c1] | —ethyl—O—methyl—O—ethyl— |
| 8b | 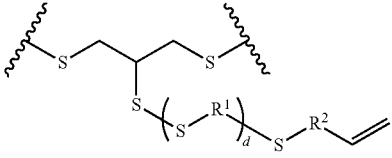 | | |

TABLE I-continued

Example polysulfide materials.

$$\text{CH}_2=\text{CH}-R^2-S-(R^1-S)_a-(\text{Linker})_c-(S-R^1)_b-S-R^2-\text{CH}=\text{CH}_2$$

| Ex. | Linker | R² | R¹ |
|---|---|---|---|
| 9a | Absent | 2,4,5-trisubstituted benzene | —ethyl—O—methyl—O—ethyl— |
| 9b | [branched thioether structure] | | |
| 10a | Absent | 3,4,5-trisubstituted benzene | —ethyl—O—methyl—O—ethyl— |
| 10b | [branched thioether structure] | | |
| 11a | Absent | 2,4-diisopropyl-5-methyl benzene derivative | —ethyl—O—methyl—O—ethyl— |
| 11b | [branched thioether structure] | | |
| 12a | Absent | 3,5-diisopropyl benzene derivative | —ethyl—O—methyl—O—ethyl— |
| 12b | [branched thioether structure] | | |

TABLE I-continued
Example polysulfide materials.
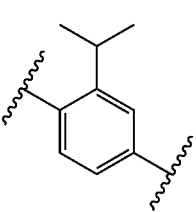 [SMILES: *c1ccc(*)c(C(C)C)c1]
| Ex. | Linker | R² | R¹ |
|---|---|---|---|
| 13a | Absent | 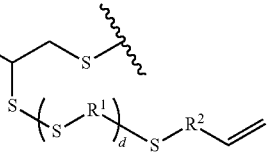 | —ethyl—O—methyl—O—ethyl— |
| 13b | 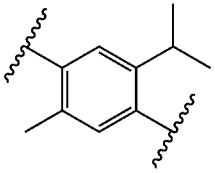 [SMILES: *c1cc(C(C)C)c(*)cc1C] | | |
| 14a | Absent | 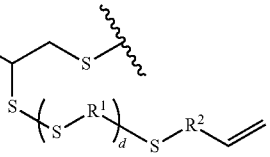 | —ethyl—O—methyl—O—ethyl— |
| 14b | 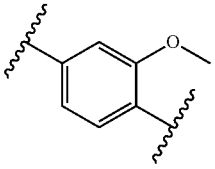 [SMILES: *c1ccc(*)c(OC)c1] | | |
| 15a | Absent | 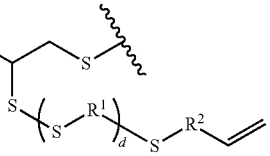 | —ethyl—O—methyl—O—ethyl— |
| 15b | 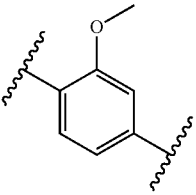 [SMILES: *c1ccc(*)c(OC)c1] | | |
| 16a | Absent |  | —ethyl—O—methyl—O—ethyl— |

TABLE I-continued

Example polysulfide materials.

$$\text{CH}_2=\text{CH}-R^2-S-(R^1-S)_a-(\text{Linker})_c-(S-R^1)_b-S-R^2-CH=CH_2$$

| Ex. | Linker | R² | R¹ |
|---|---|---|---|
| 16b | [structure: -S-CH2-CH(-S-(S-R¹)d-S-R²-CH=CH2)-CH2-S-] | | |
| 17a | Absent | [structure: benzene ring with ethoxy substituent, two attachment points] | —ethyl—O—methyl—O—ethyl— |
| 17b | [structure: -S-CH2-CH(-S-(S-R¹)d-S-R²-CH=CH2)-CH2-S-] | | |
| 18a | Absent | [structure: benzene ring with ethoxy substituent, two attachment points] | —ethyl—O—methyl—O—ethyl— |
| 18b | [structure: -S-CH2-CH(-S-(S-R¹)d-S-R²-CH=CH2)-CH2-S-] | | |
| 19a | Absent | [structure: benzene ring with two methoxy substituents, two attachment points] | —ethyl—O—methyl—O—ethyl— |
| 19b | [structure: -S-CH2-CH(-S-(S-R¹)d-S-R²-CH=CH2)-CH2-S-] | | |

TABLE I-continued

Example polysulfide materials.

$$\text{CH}_2=\text{CH}-R^2-S-(-R^1-S-)_a-(\text{Linker})_c-(-S-R^1-)_b-S-R^2-\text{CH}=\text{CH}_2$$

| Ex. | Linker | R² | R¹ |
|---|---|---|---|
| 20a | Absent | 3,5-dimethoxyphenyl (attached at 1,4 positions) | —ethyl—O—methyl—O—ethyl— |
| 20b | CH₂CH(S—(S—R¹)_d—S—R²—CH=CH₂)CH₂ branched linker | | |
| 21a | Absent | 2,5-dimethoxyphenyl (attached at 1,4 via CH₂) | —ethyl—O—methyl—O—ethyl— |
| 21b | CH₂CH(S—(S—R¹)_d—S—R²—CH=CH₂)CH₂ branched linker | | |
| 22a | Absent | 2,6-dimethoxyphenyl with CH₂ linker | —ethyl—O—methyl—O—ethyl— |
| 22b | CH₂CH(S—(S—R¹)_d—S—R²—CH=CH₂)CH₂ branched linker | | |
| 23a | Absent | 2-isopropoxyphenyl (attached at 1,4 positions) | —ethyl—O—methyl—O—ethyl— |

TABLE I-continued

Example polysulfide materials.

$$\text{CH}_2=\text{CH}-R^2-S-(R^1-S)_a-(\text{Linker})_c-(S-R^1)_b-S-R^2-\text{CH}=\text{CH}_2$$

| Ex. | Linker | R² | R¹ |
|---|---|---|---|
| 23b | [structure: CH₂-CH(S-(S-R¹)_d-S-R²-vinyl)-CH₂ with two S attachment points] | | |
| 24a | Absent | [2,4-disubstituted phenyl with OMe and OiPr groups] | —ethyl—O—methyl—O—ethyl— |
| 24b | [structure: CH₂-CH(S-(S-R¹)_d-S-R²-vinyl)-CH₂ with two S attachment points] | | |
| 25a | Absent | [3,5-disubstituted phenyl with OMe and OiPr groups, with CH₂ linker] | —ethyl—O—methyl—O—ethyl— |
| 25b | [structure: CH₂-CH(S-(S-R¹)_d-S-R²-vinyl)-CH₂ with two S attachment points] | | |
| 26a | Absent | [1,4-phenylene with CH₂ linker] | —methyl—O—methyl—O—methyl— |
| 26b | [structure: CH₂-CH(S-(S-R¹)_d-S-R²-vinyl)-CH₂ with two S attachment points] | | |
| 27a | Absent | [2-methyl-1,4-phenylene with CH₂ linker] | —methyl—O—methyl—O—methyl— |

TABLE I-continued

Example polysulfide materials.

$$\diagup\!\!\!\!\diagdown R^2-S-(R^1-S)_a-(Linker)_c-(S-R^1)_b-S-R^2\diagdown\!\!\!\!\diagup$$

| Ex. | Linker | R² | R¹ |
|---|---|---|---|
| 27b | (trisubstituted glyceryl trithioether linker with pendant —S—(S—R¹)_d—S—R²—CH=CH₂) | | |
| 28a | Absent | (2,4-disubstituted toluene-like aryl) | —ethyl—O—ethyl—O—ethyl— |
| 28b | (trisubstituted glyceryl trithioether linker with pendant —S—(S—R¹)_d—S—R²) | | |
| 29a | Absent | (2,5-disubstituted p-xylene aryl) | —ethyl—O—ethyl—O—ethyl— |
| 29b | (trisubstituted glyceryl trithioether linker with pendant —S—(S—R¹)_d—S—R²) | | |
| 30a | Absent | (2,6-dimethyl-1,4-disubstituted aryl) | —methyl—O—ethyl—O—methyl— |
| 30b | (trisubstituted glyceryl trithioether linker with pendant —S—(S—R¹)_d—S—R²) | | |
| 31a | Absent | (1,4-disubstituted phenyl) | —methyl—O—ethyl—O—methyl— |

TABLE I-continued

Example polysulfide materials.

$$\text{\Large }{\diagup\!\!\!\!\diagup}R^2-S{\left(R^1-S\right)}_a{(\text{Linker})}_c{\left(S-R^1\right)}_b S-R^2{\diagup\!\!\!\!\diagup}$$

| Ex. | Linker | R² | R¹ |
|---|---|---|---|
| 31b | [structure: glycerol trithioether branch with S—(S—R¹)_d—S—R²—vinyl] | | |
| 32a | Absent | [2,4-disubstituted toluene] | —methyl—O—ethyl—O—methyl— |
| 32b | [structure: glycerol trithioether branch with S—(S—R¹)_d—S—R²—vinyl] | | |
| 33a | Absent | [2,4-disubstituted 3-methylbenzene] | —propyl—O—methyl—O—propyl— |
| 33b | [structure: glycerol trithioether branch with S—(S—R¹)_d—S—R²—vinyl] | | |
| 34a | Absent | [2,4-disubstituted 5-methylbenzene] | —propyl—O—methyl—O—propyl— |
| 34b | [structure: glycerol trithioether branch with S—(S—R¹)_d—S—R²—vinyl] | | |
| 35a | Absent | [2,4-disubstituted 3,5-dimethylbenzene] | —propyl—O—methyl—O—propyl— |

TABLE I-continued

Example polysulfide materials.

$$\text{vinyl}-R^2-S-(R^1-S)_a-(\text{Linker})_c-(S-R^1)_b-S-R^2-\text{vinyl}$$

| Ex. | Linker | R² | R¹ |
|---|---|---|---|
| 35b | [structure: glycerol trithioether linker with pendant —S—(S—R¹)_d—S—R²—vinyl chain] | | |
| 36a | Absent | [structure: 1,2,4-trisubstituted benzene with isopropyl and methyl groups] | —ethyl—O—propyl—O—ethyl— |
| 36b | [structure: glycerol trithioether linker with pendant —S—(S—R¹)_d—S—R²—vinyl chain] | | |
| 37a | Absent | [structure: 3,5-diisopropyl-substituted benzene] | —ethyl—O—propyl—O—ethyl— |
| 37b | [structure: glycerol trithioether linker with pendant —S—(S—R¹)_d—S—R²—vinyl chain] | | |
| 38a | Absent | [structure: 2-isopropyl-1,4-disubstituted benzene] | —propyl—O—methyl—O—propyl— |
| 38b | [structure: glycerol trithioether linker with pendant —S—(S—R¹)_d—S—R²—vinyl chain] | | |

TABLE I-continued
Example polysulfide materials.
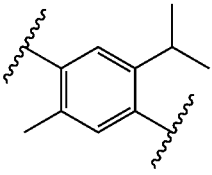 [SMILES: *c1cc(C(C)C)c(*)cc1C]
| Ex. | Linker | R² | R¹ |
|-----|--------|-----|-----|
| 39a | Absent | 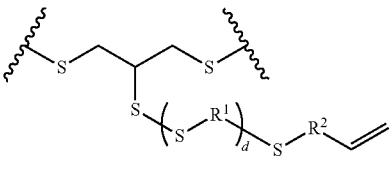 | —propyl—O—methyl—O—propyl— |
| 39b | 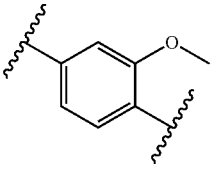 [SMILES: *c1ccc(*)c(OC)c1] | | |
| 40a | Absent |  | —propyl—O—methyl—O—propyl— |
| 40b | 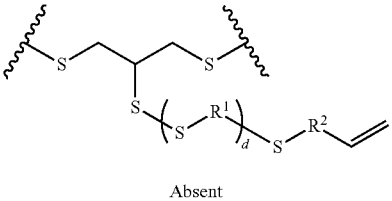 | | |
| 41a | Absent | 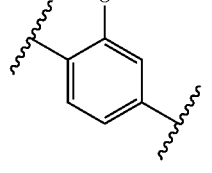 | —ethyl—O—propyl—O—ethyl— |
| 41b |  | | |
| 42a | Absent | 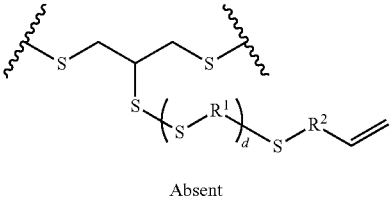 | —ethyl—O—propyl—O—ethyl— |
| 42b | 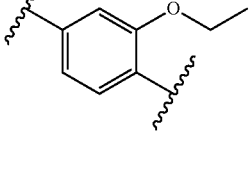 | | |

TABLE I-continued

Example polysulfide materials.

$$\text{CH}_2=\text{CH}-R^2-S-(R^1-S)_a-(\text{Linker})_c-(S-R^1)_b-S-R^2-\text{CH}=\text{CH}_2$$

| Ex. | Linker | R² | R¹ |
|---|---|---|---|
| 43a | Absent | (2-ethoxy-1,4-phenylene) | —propyl—O—methyl—O—propyl— |
| 43b | (branched trithioether linker with pendant —S—(S—R¹)_d—S—R²—CH=CH₂) | | |
| 44a | Absent | (2,5-dimethoxy-1,4-phenylene) | —ethyl—O—propyl—O—ethyl— |
| 44b | (branched trithioether linker with pendant —S—(S—R¹)_d—S—R²—CH=CH₂) | | |
| 45a | Absent | (3,5-dimethoxy-1,4-phenylene) | —ethyl—O—propyl—O—ethyl— |
| 45b | (branched trithioether linker with pendant —S—(S—R¹)_d—S—R²—CH=CH₂) | | |
| 46a | Absent | (2,5-dimethoxy-phenylene, alt. substitution) | —ethyl—O—propyl—O—ethyl— |

TABLE I-continued

Example polysulfide materials.

$$\text{\textasciitilde}R^2-S-(R^1-S)_a-(Linker)_c-(S-R^1)_b-S-R^2\text{\textasciitilde}$$

| Ex. | Linker | R² | R¹ |
|---|---|---|---|
| 46b | [structure with central CH with three S branches, one leading to S-(S-R¹)_d-S-R²] | | |
| 47a | Absent | [dimethoxy-substituted benzyl structure] | —propyl—O—methyl—O—propyl— |
| 47b | [structure with central CH with three S branches, one leading to S-(S-R¹)_d-S-R²] | | |
| 48a | Absent | [isopropoxy-substituted phenyl structure] | —ethyl—O—propyl—O—ethyl— |
| 48b | [structure with central CH with three S branches, one leading to S-(S-R¹)_d-S-R²] | | |
| 49a | Absent | [methoxy, isopropoxy-substituted phenyl structure] | —ethyl—O—ethyl—O—ethyl— |
| 49b | [structure with central CH with three S branches, one leading to S-(S-R¹)_d-S-R²] | | |

TABLE I-continued

Example polysulfide materials.

$$\diagup\!\!\!\diagdown R^2 \diagdown S \diagup\!\!\!\diagdown R^1 \diagdown S \diagdown_a (\text{Linker})_c \diagdown S \diagdown R^1 \diagdown_b S \diagdown R^2 \diagup\!\!\!\diagdown$$

| Ex. | Linker | R² | R¹ |
|---|---|---|---|
| 50a | Absent | (methoxy/isopropoxy-substituted benzyl structure) | —ethyl—O—propyl—O—ethyl— |
| 50b | (branched structure with additional —S—(S—R¹)_d—S—R²—vinyl arm) | | |

FIG. 3 depicts a second method 300 of manufacturing using a vinyl end-capped polysulfide material.

In an element 310, a vinyl end-capped polysulfide material 312 is mixed with an initiator 314 (initiator molecule). Vinyl end-capped polysulfide material 312 has a structure which corresponds to formula (I), for example. Vinyl end-capped polysulfide material 312 may be obtained by a process corresponding to the first method 200, for example.

The initiator 314 may be a free radical generating molecule activated by light (ultraviolet "UV" light, for example) and/or heat. Alternatively, the initiator 314 may be an acid generating molecule activated by light (UV light, for example) and/or heat. When the initiator 314 is a free radical generating molecule, the vinyl end groups of polysulfide material 312 may polymerize by a radical-initiated method. When the initiator 314 is an acid generating molecule (e.g., a photo-acid generator), the vinyl end groups of polysulfide material 312 may polymerize by a cationic-initiated method.

In general, loadings of initiator 314 in polysulfide material 312 may be any appropriate level, with faster curing rates typically occurring at higher loadings, but, concomitantly, molecular weights of cured materials will typically decrease with higher initiator loadings. Lower molecular weight may affect certain cured resin characteristics, such as mechanical strength and/or solvent resistance. The solubility of initiator 314 in polysulfide material 312 sets an upper loading limit. When initiator 314 is a free radical generator molecule, the amount of dissolved oxygen (or other free radical scavengers) within material 312 may effectively set the lower loading limit for initiator 314 in polysulfide material 312.

As a general matter, the molecular weight of the polysulfide material of formula (I) is preferably in a range from about 1,000 to about 20,000 g/mol for sealant and adhesive applications. In some aspects, the carbon-sulfur ratio in the polysulfide material of formula (I) is between 2:1 and 3:1 for fuel tank sealant applications.

In element 320 of the second method 300, the mixture of vinyl end-capped polysulfide material 312 and initiator 314 is applied to a component 322. Application of the resin mixture (polysulfide material 312 and initiator 314) to component 322 may include, without limitation, brushing, rolling, pouring, potting, injecting, and/or spraying. Component 322 can be a portion of a wing assembly of an aircraft or a portion of a fuselage of an aircraft, for example. In a specific example, component 322 may be used, or intended for use, as a portion of integral fuel tank of an aircraft. In another example, component 322 can be a pane of glass to be installed in a building. In still another example, component 322 can be a hull of a marine vessel (e.g., ship, boat, personal water craft, etc.).

Component 322 may be, without limitation, metal (e.g., aluminum, steel, etc.), carbon fiber, glass, stone, or concrete. Component 322 may be of any shape and size, rigid or flexible, and smooth or porous. Additional materials (e.g., other coatings, paint layers, adhesion promoters) may be between component 322 and the resin mixture.

In element 330 of the second method 300, the resin mixture of vinyl end-capped polysulfide material 312 and initiator 314 previously applied to a component 322 is cured to provide a resin 332. In an aspect of the present disclosure, element 330 may comprise a UV curing process with the curing energy supplied by a UV lamp including, for example, a mercury arc source or a light-emitting diode source. The UV curing energy may broadband or specifically selected to match an absorbance wavelength of the initiator 314. In another aspect of the present disclosure, the curing energy may be supplied by a laser, a heat gun, exposure to sunlight, indirect heating through component 322, or light at visible wavelengths or infrared wavelengths.

Initiator 314 may be specifically selected based upon the intended curing energy source or, alternatively, initiator 314 may comprise a mixture of different initiator molecules that may each respond to different curing energy sources, such as thermal initiators and photoinitiators or photoinitiators activated by different wavelengths of light.

Resin 332 may be used as sealant, a gap-filling material (e.g., caulk) and/or joining compound (e.g., adhesive). When used as a joining compound, two different components 322 (or different portions of component 322) may be joined together with resin 332 functioning as an adhesive material.

In some examples, resin 332 may optionally include various filler materials 334, such as carbon particles or fibers, clays, nylon fibers or particles, fullerenes, fused silica particles or fibers, metals, or the like. Filler materials 334 can be any shape or size and can be mixtures of different shapes and sizes. Inclusion of filler material 334 may serve to improve hardness and/or solvent resistance, reduce costs, and/or alter color of the cured resin 332. For example, filler material 334 may comprise titanium dioxide ($TiO_2$) particles or carbon black particles.

Filler material 334 may be added to the resin precursor mixture in element 310 or may be incorporated into the resin precursor mixture in element 320. For example, the filler material 334 may be a carbon fiber material placed on component 322 before application of thioether 312 and initiator 314 to component 322. Alternatively, or in addition to, filler material 334 may be nylon particles or fibers that are added to the resin precursor mixture in element 310 before application to component 322. Thus, while filler material 334 is depicted in FIG. 3 only as being in the cured resin 332, it should be understood that filler material 334 may incorporated into the resin precursor mixture at any point in the process before final curing (element 330).

In an example, component 322 may be a mold which can be removed after curing to provide a free standing resin 332 material. In such cases, component 322 may be coated with a mold-release material so as to prevent resin 332 from adhering to the surface of component 322.

In general, the curing reaction producing resin 332 in the described examples is a vinyl polymerization and not a thiol-ene reaction.

Example Synthesis

An example compound E1 having the following structure:

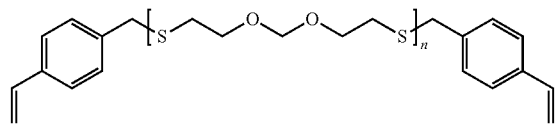

wherein n ranges from about 7 to about 38, was synthesized according to the following procedure.

Approximately 100 grams of Thiokol® LP-2 (CASRN 68611-50-7), 150 mL of a solvent, such as DMF (N,N-dimethylformamide), 0.40 g of tetrabutylammonium bromide, and 0.15 g of 4-methoxyphenol were added to a 500 mL three-necked, round bottom flask. This flask was heated while its contents were stirred. A reflux condenser was inserted into the center neck. A thermocouple probe was inserted into one side-neck, and a pressure-equalizing additional funnel was affixed to the other side neck. The mixture was heated to approximately 60° C. The addition funnel was charged with approximately 4.80 g of NaOH dissolved in 20 mL of water. This NaOH solution was added to the flask over a several minute period. The funnel was rinsed with water, and then approximately 16.50 g of 4-vinylbenzyl chloride ("VBC") was added over a several minute period. The reaction mixture was stirred for several minutes at approximately 60° C. The addition funnel was then charged with approximately 4.30 g of NaOH dissolved in 20 mL of water, and this NaOH solution was added to the flask over a several minute period. The addition funnel was rinsed with water, and then charged with approximately 8.25 g of 1-chloropropane. The 1-chloropropane was added to the flask over a several minute period, and the reaction mixture was stirred for several minutes to a few hours and then allowed to cool to room temperature.

The reaction mixture was poured from the triple neck flask into a separatory funnel charged with 50 mL of methylene chloride. The reaction flask was rinsed with 20 mL of methylene chloride which was then added to the separatory funnel. The organic layer was the lower layer and contained the desired product as a solution in methylene chloride. This organic layer was separated, and washed multiple times with distilled water. The organic layer was dried over $MgSO_4$ then filtered. The yield was approximately 83 g (c. 80% of theoretical).

UV Curing of Samples

Mixtures of the example resin product E1 from the above method and a photoinitiator molecule, ethyl (2,4,6-trimethylbenzoyl) phenylphosphinate (available commercially as Lucirin™ TPO-L from BASF), were prepared at loadings of 0.9%, 2.8%, and 5.9% (sample weights ranged from 2.8 to 3.1 g). These mixtures were poured into three adjacent wells of a 24-well polystyrene high-throughput sample plate. The plate was irradiated with broad-band UV light for 60 minutes. No precautions were taken to exclude air/oxygen. The mixtures cured, in the respective wells, to a thick skin and were allowed to stand for a few days. After this time, there was 0.35 to 0.43 inch of cured material present in each well as physically measured with a ruler.

It should be noted that the specifically described example applications and aspects are for purposes of explanation of various aspects of the present disclosure, and the potential applications and materials are not limited to the specific examples discussed herein. Other uses, applications, and variants will be apparent to those of ordinary skill in the art and these other uses, applications, and variants are contemplated and included in the present disclosure. In general, without limitation, the disclosed materials may be used in any application requiring a surface coating or adhesion between different components.

In this specification, "-alkyl-" may include, but is not limited to, an alkanediyl, which is a divalent radical derived from an aliphatic hydrocarbon. "-Alkyl-" may include, but is not limited to, a linear or branched cyclic or acyclic alkyl radical containing from 1 to about 20 carbon atoms. Furthermore, "-alkyl-" may include, but is not limited to, cycloalkanediyls and cycloalkane derived groups. In this specification, "-aryl-alkyl-" may include, but is not limited to, an aryl-substituted alkyl radical, and includes benzyl and phenylethyl. In this specification, "-aryl-" and "-heteroaryl-" may include, but is not limited to, a divalent radical derived from an aromatic molecule or a heteroaromatic molecule, respectively. "-Aryl-" may include, but is not limited to, a cyclized aromatic hydrocarbon radical and may be a monocyclic, bicyclic or tricyclic ring system. Examples of "aryl" include phenyl and naphthyl. "-Heteroaryl-" may include, but is not limited to, a radical composed of a monocyclic, bicyclic or tricyclic cyclized aromatic ring system having from 3 to about 15 ring members selected from carbon and heteroatoms including nitrogen, sulfur and oxygen, wherein at least one ring member is a heteroatom. "-Heteroarylalkyl-" may include, but is not limited to, a heteroaryl ring with an alkyl moiety attached to the heteroaryl ring, wherein the alkyl moiety is further attached to a molecular scaffold. "Halo" represents an atom from Group 17 of the periodic table, more specifically fluorine (F), chlorine (Cl), bromine (Br), and iodine (I). With respect to description related to "R$^{24}$," "alkyl" may include, but is not limited to, at least one monovalent radical derived from an aliphatic hydrocarbon, including, but not limited to, methyl, ethyl, and isopropyl substituents. With respect to description related to "R$^{24}$," "alkoxy" may include, but is not limited to, at least one monovalent radical corresponding to an ether-derived moiety, including, but not limited to, methoxy (—OCH$_3$), ethoxy (—O(CH$_2$CH$_3$), and isopropoxy (—OCH(CH$_3$)$_2$) substituents.

The descriptions of the various aspects of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A polymer of formula (I):

wherein:
each instance of R$^1$ is -alkyl-O-alkyl-O-alkyl-;
each instance of R$^2$ is the same or different and is selected from

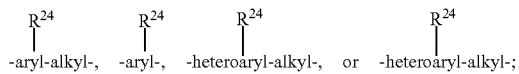
-aryl-alkyl-, -aryl-, -heteroaryl-alkyl-, or -heteroaryl-alkyl-;

each instance of R$^{24}$ is the same or different and is selected from hydrogen (H), alkyl, or alkoxy;
"Linker" is of formula (II):

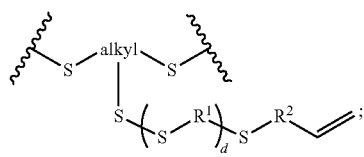

c is less than 1.0;
d is 0 when c is 0; and
a+b+d is from about 7 to about 38.

2. The polymer of claim 1, wherein each instance of R$^2$ is the same or different and is selected from -aryl-alkyl- or -aryl-.

3. The polymer of claim 2, wherein each instance of R$^2$ is the same or different and is selected from -benzyl- or -phenyl-.

4. The polymer of claim 3, wherein each instance of R$^1$ is -ethyl-O-methyl-O-ethyl-.

5. The polymer of claim 1, wherein each instance of R$^2$ is -heteroaryl-.

6. The polymer of claim 1, wherein each instance of R$^2$ is -heteroaryl-alkyl-.

7. The polymer of claim 1, wherein each instance of -alkyl- of R$^1$ is selected from the group consisting of -methyl-, -ethyl-, and -propyl-.

8. The polymer of claim 1, wherein c is greater than 0 and the Linker of formula (I) is:

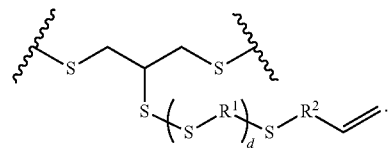

9. The polymer of claim 8, wherein each instance of R$^1$ is -ethyl-O-methyl-O-ethyl- and each instance of R$^2$ is -benzyl-.

10. The polymer of claim 8, wherein each instance of -alkyl- of R$^1$ is selected from the group consisting of -methyl-, -ethyl-, and -propyl-.

11. The polymer of claim 1, wherein c=0, and the polymer of formula (I) is selected from the group consisting of:

| Ex. | R$^2$ | R$^1$ |
|---|---|---|
| 1a | (para-phenyl-CH$_2$-) | —ethyl—O—methyl—O—ethyl— |
| 2a | (2-methyl-phenyl-CH$_2$-) | —ethyl—O—methyl—O—ethyl— |
| 3a | (methyl-phenyl-CH$_2$-) | —ethyl—O—methyl—O—ethyl— |
| 4a | (dimethyl-phenyl-CH$_2$-) | —ethyl—O—methyl—O—ethyl— |
| 5a | (dimethyl-phenyl-CH$_2$-) | —ethyl—O—methyl—O—ethyl— |
| 6a | (para-phenyl-) | —ethyl—O—methyl—O—ethyl— |

| Ex. | R² | R¹ |
|---|---|---|
| 7a | (2-methylphenyl-1,4-diyl) | —ethyl—O—methyl—O—ethyl— |
| 8a | (2-methylphenyl-1,4-diyl) | —ethyl—O—methyl—O—ethyl— |
| 9a | (2,5-dimethylphenyl-1,4-diyl) | —ethyl—O—methyl—O—ethyl— |
| 10a | (3,5-dimethylphenyl-1,4-diyl) | —ethyl—O—methyl—O—ethyl— |
| 11a | (2-isopropyl-5-methylphenyl-1,4-diyl) | —ethyl—O—methyl—O—ethyl— |
| 12a | (2-ethyl-6-isopropylphenyl-1,4-diyl) | —ethyl—O—methyl—O—ethyl— |
| 13a | (2-isopropyl-5-methylphenyl-1,4-diyl) | —ethyl—O—methyl—O—ethyl— |
| 14a | (2-isopropyl-4-methylphenyl-1,5-diyl) | —ethyl—O—methyl—O—ethyl— |
| 15a | (3-methoxyphenyl-1,4-diyl) | —ethyl—O—methyl—O—ethyl— |
| 16a | (2-methoxyphenyl-1,4-diyl) | —ethyl—O—methyl—O—ethyl— |
| 17a | (3-ethoxyphenyl-1,4-diyl) | —ethyl—O—methyl—O—ethyl— |
| 18a | (2-ethoxyphenyl-1,4-diyl) | —ethyl—O—methyl—O—ethyl— |
| 19a | (2,5-dimethoxyphenyl-1,4-diyl) | —ethyl—O—methyl—O—ethyl— |
| 20a | (3,5-dimethoxyphenyl-1,4-diyl) | —ethyl—O—methyl—O—ethyl— |
| 21a | (2,5-dimethoxyphenyl-1,4-diyl) | —ethyl—O—methyl—O—ethyl— |

-continued

| Ex. | R² | R¹ |
|---|---|---|
| 22a | [3,5-dimethoxyphenyl-CH₂-] | —ethyl—O—methyl—O—ethyl— |
| 23a | [2-isopropoxyphenyl-] | —ethyl—O—methyl—O—ethyl— |
| 24a | [2-methoxy-5-isopropoxyphenyl-] | —ethyl—O—methyl—O—ethyl— |
| 25a | [3-methoxy-5-isopropoxyphenyl-CH₂-] | —ethyl—O—methyl—O—ethyl— |
| 26a | [1,4-phenylene-CH₂-] | —methyl—O—methyl—O—methyl— |
| 27a | [2-methylphenyl-CH₂-] | —methyl—O—methyl—O—methyl— |
| 28a | [2-methylphenyl-CH₂-] | —ethyl—O—ethyl—O—ethyl— |
| 29a | [2,5-dimethylphenyl-CH₂-] | —ethyl—O—ethyl—O—ethyl— |

-continued

| Ex. | R² | R¹ |
|---|---|---|
| 30a | [2,6-dimethylphenyl-CH₂-] | —methyl—O—ethyl—O—methyl— |
| 31a | [1,4-phenylene-] | —methyl—O—ethyl—O—methyl— |
| 32a | [2-methylphenyl-] | —methyl—O—ethyl—O—methyl— |
| 33a | [2,3-dimethylphenyl-] | —propyl—O—methyl—O—propyl— |
| 34a | [2,5-dimethylphenyl-] | —propyl—O—methyl—O—propyl— |
| 35a | [3,5-dimethylphenyl-] | —propyl—O—methyl—O—propyl— |
| 36a | [2,5-diisopropylphenyl-] | —ethyl—O—propyl—O—ethyl— |
| 37a | [2,6-diisopropylphenyl-CH₂-] | —ethyl—O—propyl—O—ethyl— |

-continued

| Ex. | R² | R¹ |
|---|---|---|
| 38a | [2,4-disubstituted phenyl with isopropyl and methyl] | —propyl—O—methyl—O—propyl— |
| 39a | [2,4-disubstituted phenyl with isopropyl and methyl] | —propyl—O—methyl—O—propyl— |
| 40a | [phenyl with OMe] | —propyl—O—methyl—O—propyl— |
| 41a | [phenyl with OMe] | —ethyl—O—propyl—O—ethyl— |
| 42a | [phenyl with OEt] | —ethyl—O—propyl—O—ethyl— |
| 43a | [phenyl with OEt] | —propyl—O—methyl—O—propyl— |
| 44a | [phenyl with two OMe] | —ethyl—O—propyl—O—ethyl— |
| 45a | [phenyl with two OMe] | —ethyl—O—propyl—O—ethyl— |
| 46a | [phenyl with two OMe] | —ethyl—O—propyl—O—ethyl— |
| 47a | [phenyl with two OMe] | —propyl—O—methyl—O—propyl— |
| 48a | [phenyl with O-iPr] | —ethyl—O—propyl—O—ethyl— |
| 49a | [phenyl with OMe and O-iPr] | —ethyl—O—ethyl—O—ethyl— |
| 50a | [phenyl with OMe and O-iPr] | —ethyl—O—propyl—O—ethyl—. |

12. The polymer of claim 1, wherein c is greater than 0 and the polymer of formula (I) is selected from the group consisting of:

| Ex. | Linker | R² | R¹ |
|---|---|---|---|
| 1b | ![linker structure with S-CH2-CH(S-(S-R¹)d-S-R²-vinyl)-CH2-S] | para-phenylene-CH2 | —ethyl—O—methyl—O—ethyl— |
| 2b | ![same linker structure] | 2,4-disubstituted methylbenzene (2-methyl) | —ethyl—O—methyl—O—ethyl— |
| 3b | ![same linker structure] | 3,4-disubstituted methylbenzene | —ethyl—O—methyl—O—ethyl— |
| 4b | ![same linker structure] | 2,5-dimethyl-1,4-phenylene-CH2 | —ethyl—O—methyl—O—ethyl— |
| 5b | ![same linker structure] | 2,6-dimethyl-1,4-phenylene-CH2 | —ethyl—O—methyl—O—ethyl— |
| 6b | ![same linker structure] | 1,4-phenylene | —ethyl—O—methyl—O—ethyl— |
| 7b | ![same linker structure] | 2-methyl-1,4-phenylene | —ethyl—O—methyl—O—ethyl— |
| 8b | ![same linker structure] | 2,3-dimethyl-1,4-phenylene | —ethyl—O—methyl—O—ethyl— |
| 9b | ![same linker structure] | 2,5-dimethyl-1,4-phenylene | —ethyl—O—methyl—O—ethyl— |

-continued

| Ex. | Linker | R² | R¹ |
|---|---|---|---|
| 10b | (structure) | 3,4-dimethylphenylene | —ethyl—O—methyl—O—ethyl— |
| 11b | (structure) | 2,4,5-trimethylphenylene with isopropyl | —ethyl—O—methyl—O—ethyl— |
| 12b | (structure) | diisopropyl/ethyl phenylene | —ethyl—O—methyl—O—ethyl— |
| 13b | (structure) | isopropylphenylene | —ethyl—O—methyl—O—ethyl— |
| 14b | (structure) | methyl-isopropyl phenylene | —ethyl—O—methyl—O—ethyl— |
| 15b | (structure) | methoxyphenylene | —ethyl—O—methyl—O—ethyl— |
| 16b | (structure) | methoxyphenylene | —ethyl—O—methyl—O—ethyl— |
| 17b | (structure) | ethoxyphenylene | —ethyl—O—methyl—O—ethyl— |

-continued

| Ex. | Linker | R² | R¹ |
|---|---|---|---|
| 18b | (structure) | (2-ethoxyphenyl) | —ethyl—O—methyl—O—ethyl— |
| 19b | (structure) | (2,5-dimethoxyphenyl) | —ethyl—O—methyl—O—ethyl— |
| 20b | (structure) | (3,5-dimethoxyphenyl) | —ethyl—O—methyl—O—ethyl— |
| 21b | (structure) | (2,5-dimethoxybenzyl) | —ethyl—O—methyl—O—ethyl— |
| 22b | (structure) | (2,6-dimethoxybenzyl) | —ethyl—O—methyl—O—ethyl— |
| 23b | (structure) | (2-isopropoxyphenyl) | —ethyl—O—methyl—O—ethyl— |
| 24b | (structure) | (2-isopropoxy-5-methoxyphenyl) | —ethyl—O—methyl—O—ethyl— |

| Ex. | Linker | R² | R¹ |
|---|---|---|---|
| 25b | 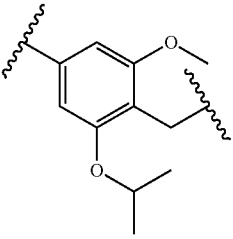 [SMILES: *Cc1c(OC)cc(*)cc1OC(C)C] | 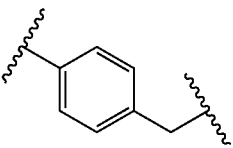 [SMILES: *Cc1ccc(*)cc1] | —ethyl—O—methyl—O—ethyl— |
| 26b | 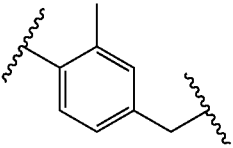 [SMILES: *Cc1ccc(*)c(C)c1] | 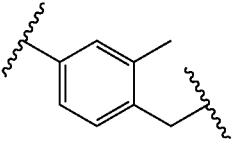 [SMILES: *Cc1ccc(*)cc1C] | —methyl—O—methyl—O—methyl— |
| 27b | 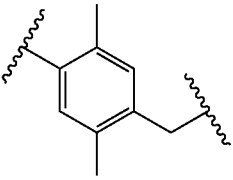 [SMILES: *Cc1cc(C)c(*)cc1C] | 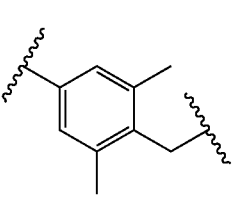 [SMILES: *Cc1c(C)cc(*)cc1C] | —methyl—O—methyl—O—methyl— |
| 28b | 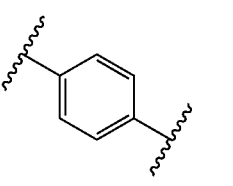 [SMILES: *c1ccc(*)cc1] | 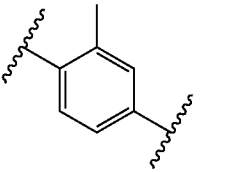 [SMILES: *c1ccc(*)c(C)c1] | —ethyl—O—ethyl—O—ethyl— |
| 29b | | | —ethyl—O—ethyl—O—ethyl— |
| 30b | | | —methyl—O—ethyl—O—methyl— |
| 31b | | | —methyl—O—ethyl—O—methyl— |
| 32b | | | —methyl—O—ethyl—O—methyl— |

-continued

| Ex. | Linker | R² | R¹ |
|---|---|---|---|
| 33b | (linker structure) | (aryl structure) | —propyl—O—methyl—O—propyl— |
| 34b | (linker structure) | (aryl structure) | —propyl—O—methyl—O—propyl— |
| 35b | (linker structure) | (aryl structure) | —propyl—O—methyl—O—propyl— |
| 36b | (linker structure) | (aryl structure) | —ethyl—O—propyl—O—ethyl— |
| 37b | (linker structure) | (aryl structure) | —ethyl—O—propyl—O—ethyl— |
| 38b | (linker structure) | (aryl structure) | —propyl—O—methyl—O—propyl— |
| 39b | (linker structure) | (aryl structure) | —propyl—O—methyl—O—propyl— |
| 40b | (linker structure) | (aryl structure) | —propyl—O—methyl—O—propyl— |

-continued

| Ex. | Linker | R² | R¹ |
|---|---|---|---|
| 41b | (linker structure) | (2-methoxy phenyl) | —ethyl—O—propyl—O—ethyl— |
| 42b | (linker structure) | (2-ethoxy phenyl) | —ethyl—O—propyl—O—ethyl— |
| 43b | (linker structure) | (2-ethoxy phenyl) | —propyl—O—methyl—O—propyl— |
| 44b | (linker structure) | (2,5-dimethoxy phenyl) | —ethyl—O—propyl—O—ethyl— |
| 45b | (linker structure) | (3,5-dimethoxy phenyl) | —ethyl—O—propyl—O—ethyl— |
| 46b | (linker structure) | (2,5-dimethoxy phenyl with methylene) | —ethyl—O—propyl—O—ethyl— |
| 47b | (linker structure) | (2,6-dimethoxy phenyl with methylene) | —propyl—O—methyl—O—propyl— |

-continued

| Ex. | Linker | R² | R¹ |
|---|---|---|---|
| 48b | | | —ethyl—O—propyl—O—ethyl— |
| 49b | | | —ethyl—O—ethyl—O—ethyl— |
| 50b | | | —ethyl—O—propyl—O—ethyl—. |

13. A method of making a polymer, comprising:
contacting, in presence of an organic solvent, at least one compound of formula (III):

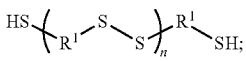  (III)

at least one compound of formula (IV):

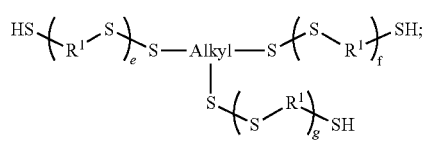  (IV)

and
at least one compound of formula (V):

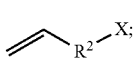  (V)

wherein:
each instance of R¹ is -alkyl-O-alkyl-O-alkyl-;
each instance of R² is the same or different and is selected from

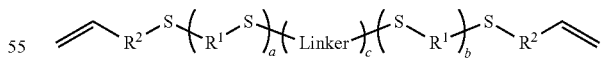

each instance of $R^{24}$ is the same or different and is selected from hydrogen (H), alkyl, or alkoxy;
X is halo;
n is from about 7 to about 38; and
e+f+g is from about 7 to about 38.

14. The method of claim 13, wherein X is chlorine, $R^2$ is -benzyl-, and at least one instance of $R^1$ is -ethyl-O-methyl-O-ethyl-.

15. The method of claim 13, wherein the organic solvent is N,N-dimethylformamide.

16. A polymer blend comprising:
a first polymer of formula (I):

(I)

wherein:
$R^1$ is -alkyl-O-alkyl-O-alkyl-,
each instance of $R^2$ is the same or different and is selected from -aryl-alkyl-, -aryl-, -heteroaryl-, or -heteroaryl-alkyl-;

each instance of R²⁴ is the same or different and is selected from hydrogen (H), alkyl, or alkoxy;
"Linker" is of formula (II):

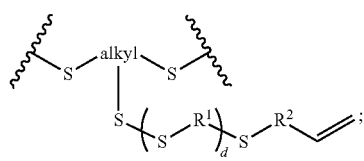

c is less than 1.0 but greater than 0, and
a+b+d is from about 7 to about 38; and
a second polymer of formula (I):

wherein:
R¹ is -alkyl-O-alkyl-O-alkyl-,
each instance of R² is the same or different and is selected from -aryl-alkyl-,   -aryl-,   -heteroaryl-,   or   -heteroaryl-alkyl-;
(each with R²⁴ substituent)

each instance of R²⁴ is the same or different and is selected from hydrogen (H), alkyl, or alkoxy;
"Linker" is of formula (II):

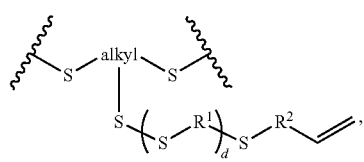

c=0, d=0, and
a+b is from about 7 to about 38.

17. The polymer blend of claim 16, wherein the first polymer of formula (I) is:

wherein:
n ranges from about 7 to about 38,
each instance of R²⁴ is the same or different and is selected from H, alkyl, or alkoxy; and
wherein the second polymer of formula (I) is:

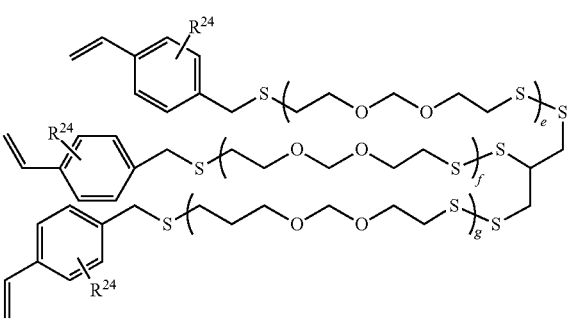

wherein:
e+f+g ranges from about 7 to about 38, and
each instance of R²⁴ is the same or different and is selected from H, alkyl, or alkoxy.

18. The polymer blend of claim 16, wherein 'c' is greater than 0 and the first polymer of formula (I) is selected from the group consisting of:

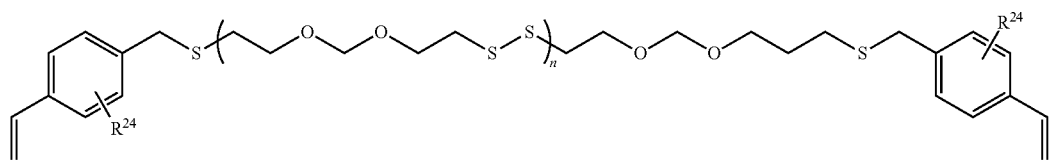

| Ex. | Linker | R² | R¹ |
|---|---|---|---|
| 1b | ~S-CH2-CH(S-(S-R¹)d-S-R²-CH=CH2)-CH2-S~ | 1,4-phenylene-CH2 | —ethyl—O—methyl—O—ethyl— |
| 2b | ~S-CH2-CH(S-(S-R¹)d-S-R²-CH=CH2)-CH2-S~ | 2-methyl-1,4-phenylene-CH2 | —ethyl—O—methyl—O—ethyl— |
| 3b | ~S-CH2-CH(S-(S-R¹)d-S-R²-CH=CH2)-CH2-S~ | 3-methyl-1,4-phenylene-CH2 | —ethyl—O—methyl—O—ethyl— |
| 4b | ~S-CH2-CH(S-(S-R¹)d-S-R²-CH=CH2)-CH2-S~ | 2,5-dimethyl-1,4-phenylene-CH2 | —ethyl—O—methyl—O—ethyl— |
| 5b | ~S-CH2-CH(S-(S-R¹)d-S-R²-CH=CH2)-CH2-S~ | 2,6-dimethyl-1,4-phenylene-CH2 | —ethyl—O—methyl—O—ethyl— |
| 6b | ~S-CH2-CH(S-(S-R¹)d-S-R²-CH=CH2)-CH2-S~ | 1,4-phenylene | —ethyl—O—methyl—O—ethyl— |
| 7b | ~S-CH2-CH(S-(S-R¹)d-S-R²-CH=CH2)-CH2-S~ | 2-methyl-1,4-phenylene | —ethyl—O—methyl—O—ethyl— |
| 8b | ~S-CH2-CH(S-(S-R¹)d-S-R²-CH=CH2)-CH2-S~ | 3-methyl-1,4-phenylene | —ethyl—O—methyl—O—ethyl— |
| 9b | ~S-CH2-CH(S-(S-R¹)d-S-R²-CH=CH2)-CH2-S~ | 2,5-dimethyl-1,4-phenylene | —ethyl—O—methyl—O—ethyl— |

| Ex. | Linker | R² | R¹ |
|---|---|---|---|
| 10b | (structure) | 3,4-dimethylphenylene | —ethyl—O—methyl—O—ethyl— |
| 11b | (structure) | 2,5-diisopropyl-4-methylphenylene | —ethyl—O—methyl—O—ethyl— |
| 12b | (structure) | 2,6-diisopropylphenylene | —ethyl—O—methyl—O—ethyl— |
| 13b | (structure) | 2-isopropylphenylene | —ethyl—O—methyl—O—ethyl— |
| 14b | (structure) | 2-isopropyl-5-methylphenylene | —ethyl—O—methyl—O—ethyl— |
| 15b | (structure) | 2-methoxyphenylene | —ethyl—O—methyl—O—ethyl— |
| 16b | (structure) | 3-methoxyphenylene | —ethyl—O—methyl—O—ethyl— |
| 17b | (structure) | 2-ethoxyphenylene | —ethyl—O—methyl—O—ethyl— |

-continued

| Ex. | Linker | R² | R¹ |
|---|---|---|---|
| 18b | (linker structure) | (2-ethoxyphenyl, 1,4-disubstituted) | —ethyl—O—methyl—O—ethyl— |
| 19b | (linker structure) | (2,5-dimethoxyphenyl, 1,4-disubstituted) | —ethyl—O—methyl—O—ethyl— |
| 20b | (linker structure) | (2,6-dimethoxyphenyl, 1,4-disubstituted) | —ethyl—O—methyl—O—ethyl— |
| 21b | (linker structure) | (2,5-dimethoxybenzyl) | —ethyl—O—methyl—O—ethyl— |
| 22b | (linker structure) | (2,6-dimethoxybenzyl) | —ethyl—O—methyl—O—ethyl— |
| 23b | (linker structure) | (2-isopropoxyphenyl, 1,4-disubstituted) | —ethyl—O—methyl—O—ethyl— |
| 24b | (linker structure) | (2-methoxy-5-isopropoxyphenyl) | —ethyl—O—methyl—O—ethyl— |

-continued

| Ex. | Linker | R² | R¹ |
|---|---|---|---|
| 25b | ![linker structure] | ![aryl with OMe and OiPr] | —ethyl—O—methyl—O—ethyl— |
| 26b | ![linker structure] | ![1,4-phenylene] | —methyl—O—methyl—O—methyl— |
| 27b | ![linker structure] | ![dimethyl phenylene] | —methyl—O—methyl—O—methyl— |
| 28b | ![linker structure] | ![methyl phenylene] | —ethyl—O—ethyl—O—ethyl— |
| 29b | ![linker structure] | ![dimethyl phenylene] | —ethyl—O—ethyl—O—ethyl— |
| 30b | ![linker structure] | ![dimethyl phenylene] | —methyl—O—ethyl—O—methyl— |
| 31b | ![linker structure] | ![1,4-phenylene] | —methyl—O—ethyl—O—methyl— |
| 32b | ![linker structure] | ![methyl phenylene] | —methyl—O—ethyl—O—methyl— |

-continued

| Ex. | Linker | R² | R¹ |
|---|---|---|---|
| 33b | [structure: S-CH2-CH(S-(S-R¹)d-S-R²-vinyl)-CH2-S] | [1,4-disubstituted 2-methylbenzene] | —propyl—O—methyl—O—propyl— |
| 34b | [structure: S-CH2-CH(S-(S-R¹)d-S-R²-vinyl)-CH2-S] | [1,4-disubstituted 2,5-dimethylbenzene] | —propyl—O—methyl—O—propyl— |
| 35b | [structure: S-CH2-CH(S-(S-R¹)d-S-R²-vinyl)-CH2-S] | [1,3-disubstituted 4,5-dimethylbenzene] | —propyl—O—methyl—O—propyl— |
| 36b | [structure: S-CH2-CH(S-(S-R¹)d-S-R²-vinyl)-CH2-S] | [disubstituted diisopropyl-dimethylbenzene] | —ethyl—O—propyl—O—ethyl— |
| 37b | [structure: S-CH2-CH(S-(S-R¹)d-S-R²-vinyl)-CH2-S] | [disubstituted diisopropyl-benzene] | —ethyl—O—propyl—O—ethyl— |
| 38b | [structure: S-CH2-CH(S-(S-R¹)d-S-R²-vinyl)-CH2-S] | [isopropyl-substituted benzene] | —propyl—O—methyl—O—propyl— |
| 39b | [structure: S-CH2-CH(S-(S-R¹)d-S-R²-vinyl)-CH2-S] | [isopropyl-methyl-substituted benzene] | —propyl—O—methyl—O—propyl— |
| 40b | [structure: S-CH2-CH(S-(S-R¹)d-S-R²-vinyl)-CH2-S] | [methoxy-substituted benzene] | —propyl—O—methyl—O—propyl— |

-continued

| Ex. | Linker | R² | R¹ |
|---|---|---|---|
| 41b | (structure) | (2-methoxy-1,4-phenylene) | —ethyl—O—propyl—O—ethyl— |
| 42b | (structure) | (2-ethoxy-1,4-phenylene) | —ethyl—O—propyl—O—ethyl— |
| 43b | (structure) | (2-ethoxy-1,4-phenylene) | —propyl—O—methyl—O—propyl— |
| 44b | (structure) | (2,5-dimethoxy-1,4-phenylene) | —ethyl—O—propyl—O—ethyl— |
| 45b | (structure) | (3,5-dimethoxy-1,4-phenylene) | —ethyl—O—propyl—O—ethyl— |
| 46b | (structure) | (2,5-dimethoxy-benzyl substituted) | —ethyl—O—propyl—O—ethyl— |
| 47b | (structure) | (2,6-dimethoxy-benzyl substituted) | —propyl—O—methyl—O—propyl— |

| Ex. | Linker | R² | R¹ |
|---|---|---|---|
| 48b | [structure: CH₂-S, CH-S, CH₂-S branched with -(S-R¹)d-S-R²- chain ending in vinyl] | [structure: benzene with isopropoxy at ortho position, two attachment points] | —ethyl—O—propyl—O—ethyl— |
| 49b | [structure: CH₂-S, CH-S, CH₂-S branched with -(S-R¹)d-S-R²- chain ending in vinyl] | [structure: benzene with methoxy and isopropoxy substituents, two attachment points] | —ethyl—O—ethyl—O—ethyl— |
| 50b | [structure: CH₂-S, CH-S, CH₂-S branched with -(S-R¹)d-S-R²- chain ending in vinyl] | [structure: benzene with methoxy and isopropoxy substituents, two attachment points] | —ethyl—O—propyl—O—ethyl—. |

19. The polymer blend of claim 16, wherein 'c' is 0 and the second polymer of formula (I) is selected from the group consisting of:

| Ex. | R² | R¹ |
|---|---|---|
| 1a | [para-disubstituted benzene] | —ethyl—O—methyl—O—ethyl— |
| 2a | [benzene with methyl substituent] | —ethyl—O—methyl—O—ethyl— |
| 3a | [benzene with methyl substituent] | —ethyl—O—methyl—O—ethyl— |
| 4a | [benzene with two methyl substituents] | —ethyl—O—methyl—O—ethyl— |
| 5a | [benzene with two methyl substituents] | —ethyl—O—methyl—O—ethyl— |
| 6a | [para-disubstituted benzene] | —ethyl—O—methyl—O—ethyl— |
| 7a | [benzene with methyl substituent] | —ethyl—O—methyl—O—ethyl— |
| 8a | [benzene with methyl substituent] | —ethyl—O—methyl—O—ethyl— |

-continued

| Ex. | R² | R¹ |
|---|---|---|
| 9a | (2,5-dimethylphenylene) | —ethyl—O—methyl—O—ethyl— |
| 10a | (3,5-dimethylphenylene) | —ethyl—O—methyl—O—ethyl— |
| 11a | (2,5-diisopropyl... phenylene) | —ethyl—O—methyl—O—ethyl— |
| 12a | (3,4-diethylphenylene) | —ethyl—O—methyl—O—ethyl— |
| 13a | (2-isopropylphenylene) | —ethyl—O—methyl—O—ethyl— |
| 14a | (2-isopropyl-5-methylphenylene) | —ethyl—O—methyl—O—ethyl— |
| 15a | (3-methoxyphenylene) | —ethyl—O—methyl—O—ethyl— |
| 16a | (2-methoxyphenylene) | —ethyl—O—methyl—O—ethyl— |
| 17a | (2-ethoxyphenylene) | —ethyl—O—methyl—O—ethyl— |

-continued

| Ex. | R² | R¹ |
|---|---|---|
| 18a | (2-ethoxyphenylene) | —ethyl—O—methyl—O—ethyl— |
| 19a | (2,5-dimethoxyphenylene) | —ethyl—O—methyl—O—ethyl— |
| 20a | (3,5-dimethoxyphenylene) | —ethyl—O—methyl—O—ethyl— |
| 21a | (2,5-dimethoxyphenylene) | —ethyl—O—methyl—O—ethyl— |
| 22a | (2,6-dimethoxyphenylene) | —ethyl—O—methyl—O—ethyl— |
| 23a | (2-isopropoxyphenylene) | —ethyl—O—methyl—O—ethyl— |
| 24a | (2-methoxy-5-isopropoxyphenylene) | —ethyl—O—methyl—O—ethyl— |
| 25a | (2-methoxy-6-isopropoxyphenylene) | —ethyl—O—methyl—O—ethyl— |

| Ex. | R² | R¹ |
|---|---|---|
| 26a | 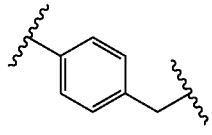 [SMILES: *Cc1ccc(*)cc1] | —methyl—O—methyl—O—methyl— |
| 27a | 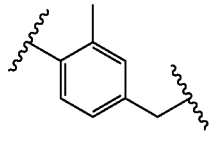 [SMILES: *Cc1ccc(*)c(C)c1] | —methyl—O—methyl—O—methyl— |
| 28a | 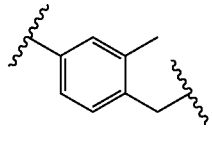 [SMILES: *Cc1ccc(*)cc1C] | —ethyl—O—ethyl—O—ethyl— |
| 29a | 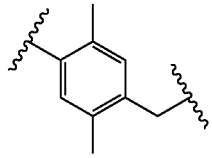 [SMILES: *Cc1cc(C)c(*)cc1C] | —ethyl—O—ethyl—O—ethyl— |
| 30a | 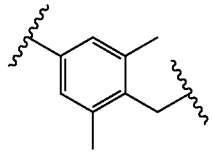 [SMILES: *Cc1c(C)cc(*)cc1C] | —methyl—O—ethyl—O—methyl— |
| 31a | 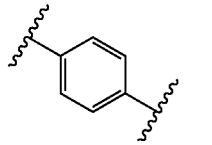 [SMILES: *c1ccc(*)cc1] | —methyl—O—ethyl—O—methyl— |
| 32a | 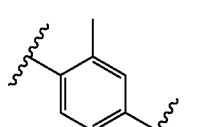 | —methyl—O—ethyl—O—methyl— |
| 33a | 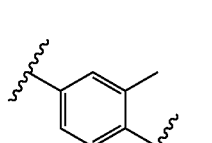 | —propyl—O—methyl—O—propyl— |
| 34a | 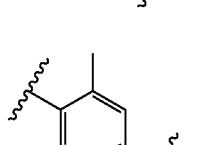 | —propyl—O—methyl—O—propyl— |
| 35a | 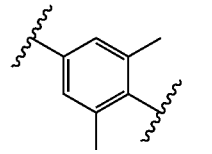 [SMILES: *c1cc(C)c(*)c(C)c1] | —propyl—O—methyl—O—propyl— |
| 36a | 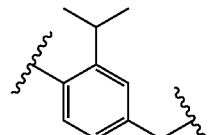 | —ethyl—O—propyl—O—ethyl— |
| 37a | 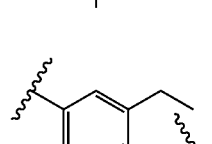 | —ethyl—O—propyl—O—ethyl— |
| 38a | 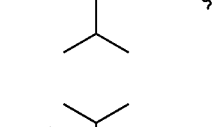 | —propyl—O—methyl—O—propyl— |
| 39a | 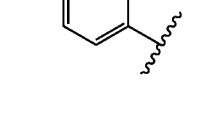 | —propyl—O—methyl—O—propyl— |
| 40a | 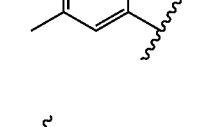 | —propyl—O—methyl—O—propyl— |
| 41a | 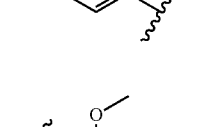 | —ethyl—O—propyl—O—ethyl— |
| 42a | 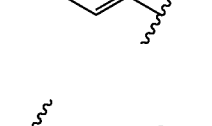 | —ethyl—O—propyl—O—ethyl— |

-continued

| Ex. | R² | R¹ |
|---|---|---|
| 43a | [ethoxy-substituted phenyl] | —propyl—O—methyl—O—propyl— |
| 44a | [dimethoxy-substituted phenyl] | —ethyl—O—propyl—O—ethyl— |
| 45a | [dimethoxy-substituted phenyl] | —ethyl—O—propyl—O—ethyl— |
| 46a | [dimethoxy-substituted phenyl] | —ethyl—O—propyl—O—ethyl— |
| 47a | [dimethoxy-substituted phenyl] | —propyl—O—methyl—O—propyl— |
| 48a | [isopropoxy-substituted phenyl] | —ethyl—O—propyl—O—ethyl— |
| 49a | [methoxy-isopropoxy phenyl] | —ethyl—O—ethyl—O—ethyl— |
| 50a | [methoxy-isopropoxy phenyl] | —ethyl—O—propyl—O—ethyl—. |

* * * * *

UNITED STATES PATENT AND TRADEMARK OFFICE
CERTIFICATE OF CORRECTION

PATENT NO. : 9,751,966 B2
APPLICATION NO. : 14/924079
DATED : September 5, 2017
INVENTOR(S) : Andrew M. Zweig It is certified that error appears in the above-identified patent and that said Letters Patent is hereby corrected as shown below:

In Column 39, Lines 38-40, in Claim 1, delete "  " and insert -- 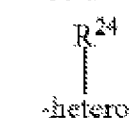 --, therefor.

In Column 60, Lines 35-37, in Claim 13, delete " 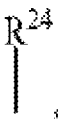 " and insert -- 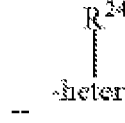 --, therefor.

Signed and Sealed this
Seventh Day of November, 2017

Joseph Matal
*Performing the Functions and Duties of the
Under Secretary of Commerce for Intellectual Property and
Director of the United States Patent and Trademark Office*